(12) United States Patent
Fabo et al.

(10) Patent No.: US 9,393,341 B2
(45) Date of Patent: Jul. 19, 2016

(54) STIFFENING LAYER FOR FACILITATING APPLICATION OF A PLASTIC FILM TO SKIN

(75) Inventors: Tomas Fabo, Molnlycke (SE); Anna Svensby, Vastra Frolunda (SE)

(73) Assignee: Mölnlycke Health Care AB, Göteborg (SE)

( * ) Notice: Subject to any disclaimer, the term of this patent is extended or adjusted under 35 U.S.C. 154(b) by 350 days.

(21) Appl. No.: 12/811,243

(22) PCT Filed: Feb. 6, 2009

(86) PCT No.: PCT/SE2009/050121
§ 371 (c)(1),
(2), (4) Date: Sep. 30, 2010

(87) PCT Pub. No.: WO2009/110836
PCT Pub. Date: Sep. 11, 2009

(65) Prior Publication Data
US 2011/0015556 A1    Jan. 20, 2011

(30) Foreign Application Priority Data

Mar. 7, 2008   (SE) ...................................... 0800543

(51) Int. Cl.
*A61L 15/42*   (2006.01)
*A61F 13/00*   (2006.01)
*A61F 13/02*   (2006.01)
(Continued)

(52) U.S. Cl.
CPC ......... *A61L 15/425* (2013.01); *A61F 13/00085* (2013.01); *A61F 13/02* (2013.01); *A61L 15/24* (2013.01); *A61L 15/26* (2013.01); *A61F 2013/00302* (2013.01); *A61F 2013/00587* (2013.01); *A61F 2013/00829* (2013.01)

(58) Field of Classification Search
USPC ............................. 602/41–59; 128/888–889;
206/440–441; 424/445, 473
See application file for complete search history.

(56) References Cited

U.S. PATENT DOCUMENTS

| 4,706,662 | A |   | 11/1987 | Thompson |           |
|-----------|---|---|---------|----------|-----------|
| 4,813,942 | A | * | 3/1989  | Alvarez  | ......... A61F 13/02 |
|           |   |   |         |          | 424/445   |
| 5,000,172 | A |   | 3/1991  | Ward     |           |

(Continued)

FOREIGN PATENT DOCUMENTS

| CN | 101925336 | 12/2010 |
|----|-----------|---------|
| EP | 0 051 935 | 5/1982  |

(Continued)

OTHER PUBLICATIONS

International Search Report dated Jun. 15, 2009, from corresponding PCT application.

(Continued)

*Primary Examiner* — Ophelia A Hawthorne
(74) *Attorney, Agent, or Firm* — Ballard Spahr LLP

(57) ABSTRACT

A stiffening layer for facilitating application of a plastic film to skin, the plastic film being a component in a wound dressing or other medical device and having the stiffening layer removably attached to one side thereof, at least a part of the other side of the film being provided with a layer of self-adhering adhesive. The stiffening layer is made of a stretchable material having a thickness of between 0.5-10 mm. The stiffening layer covers the whole area of the film and is divided into two or more portions by cutting line or lines.

18 Claims, 1 Drawing Sheet

(51) Int. Cl.
*A61L 15/24* (2006.01)
*A61L 15/26* (2006.01)

(56) References Cited

U.S. PATENT DOCUMENTS

| | | | |
|---|---|---|---|
| 5,160,315 A | | 11/1992 | Heinecke et al. |
| 5,266,371 A | * | 11/1993 | Sugii et al. ............... 428/41.5 |
| 5,618,276 A | * | 4/1997 | Leise, Jr. ............. A61F 5/443 |
| | | | 604/336 |
| 5,733,251 A | | 3/1998 | Johns |
| 5,755,681 A | * | 5/1998 | Plews .................. A61F 13/023 |
| | | | 602/52 |
| 5,840,052 A | * | 11/1998 | Johns ........................ 602/54 |
| 5,891,077 A | * | 4/1999 | Gilman et al. ................ 602/57 |
| 5,973,221 A | * | 10/1999 | Collyer ............ A61F 13/00034 |
| | | | 602/46 |
| 6,043,408 A | | 3/2000 | Geng |
| 6,165,156 A | * | 12/2000 | Cesarczyk et al. ............ 604/180 |
| 6,169,224 B1 | * | 1/2001 | Heinecke et al. ............... 602/58 |
| 6,217,508 B1 | * | 4/2001 | Ball et al. ........................ 600/25 |
| 6,479,724 B1 | * | 11/2002 | Areskoug ............... A61F 13/02 |
| | | | 602/41 |
| 2008/0114278 A1 | | 5/2008 | Fabo |
| 2008/0312574 A1 | * | 12/2008 | Pernot .................. A61F 13/023 |
| | | | 602/52 |
| 2009/0062754 A1 | * | 3/2009 | Tang .............................. 604/307 |

FOREIGN PATENT DOCUMENTS

| | | |
|---|---|---|
| EP | 0 870 488 | 10/1998 |
| EP | 2249760 | 2/2009 |
| FR | 2 893 249 | 5/2007 |
| GB | 2249266 A * | 5/1992 |
| WO | 93/07841 | 4/1993 |
| WO | 2006/075950 | 7/2006 |
| WO | 2008/019310 | 2/2008 |
| WO | WO/2009/110836 | 9/2009 |

OTHER PUBLICATIONS

International Preliminary Report on Patentability issued Sep. 7, 2010 by the International Search Authority for Application PCT/SE2009/050121 filed Feb. 6, 2009 (Applicant—Molnlycke Health Care AB // Inventor—Tomas Fabo; pp. 1-6).

Written Opinion issued Jun. 15, 2009 by the International Search Authority for Application PCT/SE2009/050121 filed Feb. 6, 2009 (Applicant—Molnlycke Health Care AB // Inventor—Tomas Fabo; pp. 1-5).

Search Report issued on Dec. 11, 2012 for European Patent Application No. EP 09716951.0, which was filed on Feb. 6, 2009 [Inventor—Fabo; Applicant—Molnlycke Health Care AB] [4 pages].

* cited by examiner

STIFFENING LAYER FOR FACILITATING APPLICATION OF A PLASTIC FILM TO SKIN

TECHNICAL FIELD

The present invention relates to a stiffening layer for facilitating application of a plastic film to skin, said plastic film being a component in a wound dressing or other medical device and having said stiffening layer removably attached to one side thereof, at least a part of the other side of said film being provided with a layer of self-adhering adhesive, said stiffening layer being made of a stretchable material having a thickness of between 0.5-10 mm stiffening layer for facilitating application of a plastic film to skin, as well as a medical device provided with such a stiffening layer.

BACKGROUND TO THE INVENTION

Wound dressings including a thin plastic film having an adhesive coating on one side are relatively widely used and adhesively coated thin plastic films are also used to affix medical devices other than wound dressings to the skin of a person, such as e.g. ostomy bags. A problem with thin adhesively coated plastic films is their tendency to wrinkle and adhere to themselves which make them very difficult to handle. In order to make such film dressings easier to apply to the skin of a person, they are provided with temporary stiffening layers which are removed once the film dressing has been applied. It is very difficult to apply film dressings without such stiffening layers. Known stiffening layers consist of paper (possibly silicone coated), plastic films or laminates of these materials.

EP 051935 describes a dressing made of polymeric film and a releasable layer made of paper providing stiffness to the dressing. U.S. Pat. No. 5,160,315 suggests kraft papers, polyethylene, polypropylene, polyester and composites of those materials as suitable materials for stiffening layers. The materials suggested provide stiffness to flexible film dressings but do not provide any guidance on choice of materials to solve the problem of conformability and difficulty in application to e.g. uneven body parts.

The more recent WO2008/019310 on the other hand presents a complex multi-layer conformable wound dressing having a permanently attached (i.e. not removable) support layer for application of the dressing to e.g. convex surfaces.

Even if existing stiffening layers make it possible to apply film dressings, usually without great problems, there is a relatively large risk of failure, creating of folds in the film when a film dressing is to be applied to uneven parts of the body of a person, such as heels, hands or elbows or even detachment of the dressing when it is worn.

EP 0 870 488 A2 discloses a foraminous stiffening layer having a multiplicity of wide openings separated by strips of stiffening material, whereby several of said strips have free ends along a peripheral edge of the film. Such a stiffening layer has many advantages but must be carefully handled during application due to the lack of stiffening strips between the free ends of such strips along at least two opposite peripheral edges of the film.

The objective of the present invention is to improve such removable stiffening layers in wound dressings or other medical devices so that such devices are more easy to apply and so that the risk of failure or the creating of folds when the dressing or the medical device is applied to skin is eliminated or at least greatly reduced.

SUMMARY OF THE INVENTION

This objective is accomplished by a stiffening layer for facilitating application of a plastic film to skin, said plastic film being a component in a wound dressing or other medical device and having said stiffening layer removably attached to one side thereof, at least a part of the other side of said film being provided with a layer of self-adhering adhesive, said stiffening layer being made of a stretchable material having a thickness of between 0.5-10 mm, characterised in that .said stiffening layer covers the whole area of the film and is divided into two or more portions by cutting line or lines. A stretchable stiffening layer has far better ability to conform its shape to the shape of an uneven portion of the body of a person than a non-stretchable layer, such as the paper or plastic layers commonly used, and since the thickness of the stiffening layer is chosen so that the bending strength of the stiffening layer will be in the same range as for such conventional stiffening layers, the stiffness of a stiffening layer according to the present invention will still facilitate handling of a thin film of a wound dressing or other medical device before application thereof to the same degree as conventional stiffening layers. By the covering of the whole area of the film it is ensured that an adequate stiffening of the film is obtained even if the initial dressing would be cut to a smaller size. By dividing the stiffening layer into two or more portions the application of the film can be performed stepwise and portions of the stiffening layer can be taken away in order to enable visual observation.

According to a first preferred embodiment the stiffening layer includes a porous layer with a porosity of at least 80%, preferably at least 90% and more preferably at least 95%.

The stretchability of the stiffening layer should be less than 2000 $kN/m^2$, preferably less than 1000 $kN/m^2$, more preferably less than 500 $kN/m^2$, and most preferably less than 250 $kN/m^2$ measured as the axial nominal stress at 5% elongation.

Preferably, the stiffening layer consists of elastic material. In the most preferred embodiment it consists of polymeric foam, such as a polyurethane foam or a polyethylene foam. Of advantage is that the foam has closed cells, since the adhesion of the foam to a film of a wound dressing or other medical device is easier to control for foam with closed cells than foam with open cells.

According to a second embodiment the stiffening layer includes a layer of fibrous material. The stiffening layer can be a single layer or a laminate of two or more layers. If the stiffening layer includes a first layer of fibrous material or polymeric foam with open pores, a second layer of plastic film is of advantage laminated to the first layer in order to facilitate controlling of the adhesion of the stiffening layer to a plastic film.

The invention also relates to a wound dressing or other medical device, exemplified but not limited to ostomy bandages, surgical drapes, cannula fixation devices or medical tapes, including a plastic film and a stiffening layer removably attached to one side thereof, at least a part of the other side of said film being provided with a layer of self-adhering adhesive, characterised in that said stiffening layer is a stiffening layer described above in relation to the present invention.

In such a wound dressing or other medical device the stiffening layer has been removably attached to the film by application of heat and/or pressure or by a layer of adhesive.

BRIEF DESCRIPTION OF THE DRAWING

The invention will now be described with reference to the enclosed figures, of which.

DESCRIPTION OF EMBODIMENTS

Figure 1:
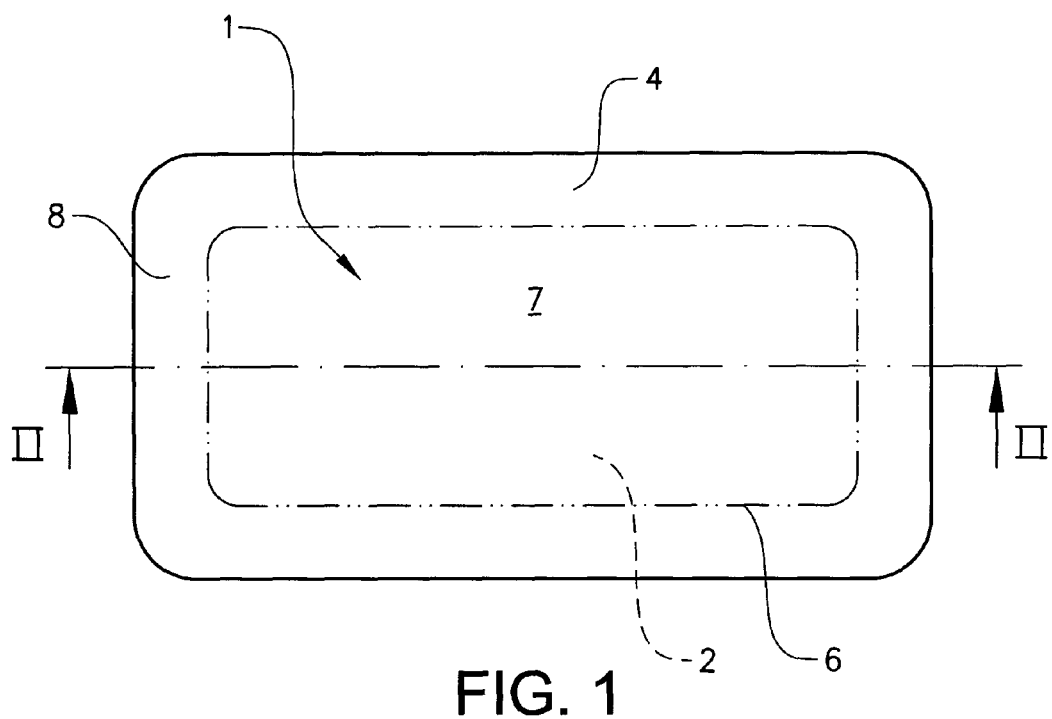
FIG. 1 schematically shows a top view of a wound dressing according to a first preferred embodiment of the invention.
Figure 2:
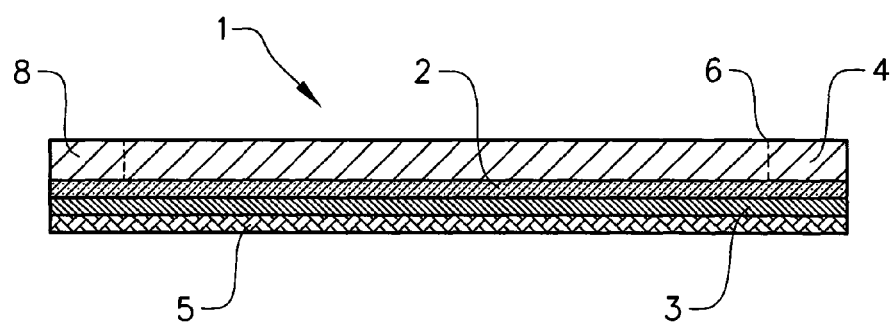
FIG. 2 shows a sectional view along line II-II in FIG. 1.

In FIGS. 1 and 2 a wound dressing 1 according to a first preferred embodiment of the present invention is schematically shown. The wound dressing 1 includes a thin plastic film layer 2 preferably made of polyurethane plastic, which is coated with a layer 3 of a soft, skin friendly adhesive. The thickness of the plastic film preferably lies between 12 and 25 micrometres, and is less than 50 micrometres in any case.

A stiffening layer 4 is also applied above the film layer 2, that is to say on the opposite side to the adhesive layer 3. The adhesive layer 3 is protected in a customary fashion by a protective layer 5 of a material with low adhesion to the adhesive, for example polyethylene-coated paper, silicone-coated paper, silicone-coated film or polyethylene film, which protective layer is removed before application of wound dressing 1. The function of the stiffening layer is to stiffen up the wound dressing 1 in order to facilitate application of the dressing. Without a stiffening layer it would be very difficult to handle the thin film layer 2 with its coating of adhesive after that the protective layer has been removed.

In conjunction with the application of the film dressing 2, 3, the protective layer 5 is first removed, after which the dressing is positioned on the user's skin and pressed securely onto the skin. Finally, the stiffening layer 4 is removed. The protective layer 5 can consist of several parts enabling sequential application of parts of film dressing to skin. Moreover, the protective layer may have protrusions in contact with the adhesive layer to decrease the surface area to which it adheres and thereby facilitate removal.

A principal function of the adhesive coating 3 is to attach the film dressing 1 securely to the skin, so that the product remains in place during the normal loadings which film dressings are subjected to. Another function of the adhesive coating 3 is to attach the film dressing 1 tightly to the skin of the patient, so that fluid-borne transport of bacteria in any direction between the skin and the adhesive coating is prevented.

The adhesive in the coating must also be skin friendly and must permit removal of the film dressings without causing damage to the skin.

A silicone gel possesses low surface energy, and it adapts very well to the skin, that is to say it flows out into any unevennesses in the skin and creates a large contact surface between the skin and the soft silicone gel. This large contact surface helps the silicone gel to become attached securely to the skin, in spite of the fact that the strength of the adhesive attachment of the silicone gel to the skin in itself is not so strong. The adhesive strength constitutes a measure of the energy required in order to separate/pull off the adhesive layer from the skin. A contributory factor to the fact that high energy, and thus a high pulling force, is required in order to remove the silicone gel from the skin, in spite of the relatively weak strength of the adhesive attachment, is that a lot of energy is consumed in stretching the soft silicone gel before it releases from the skin. The softer and thicker the layer of silicone gel, the greater the force/energy required to remove the gel from the skin. Examples of suitable silicone gels and methods of measuring softness and adhesion can be found in WO 2006/075950 to which is referred in this respect.

For these reasons silicone gels are preferably used for the adhesive layer 3.

The stiffening layer 4 is made of a polymeric foam, for example polyethylene foam or polyurethane foam. Such material has, in contrast to known materials for stiffening layers, the ability to follow the shape of an uneven body portion of a person to which the wound dressing should be applied, such as a heel, a hand, a knee or an elbow. This is due to the fact that polymeric foams are stretchable and can be applied for example to a heel which much less risk of creating folds than with known film dressings.

The stretchability of the foam shall be less than 2000 kN/m$^2$, preferably less than 1000 kN/m$^2$, more preferably less than 500 kN/m$^2$, and most preferably less than 250 kN/m$^2$ measured as the axial nominal stress at 5% elongation. To determine the axial (nominal) stress, the Method ASTM D 882-02 was used to measure the tensile force P. For determination of the material thickness D, the SS-EN: ISO 9073-2 Method A: 1996 was used. The axial nominal stress S was then obtained by the following calculation S=P/(D*W), where W is the sample width.

In contrast to polymeric films and paper, polymeric foam is also compressible, a property that also contributes to reduce the risk for folds to occur when the dressing is applied. By the term "compressible" is primarily meant the reduction of the pore volumes when the foam is subjected to external pressure.

Since the stiffening layer 4 also must perform the task of holding the film layer 2 with its layer of adhesive 3 flat and stretched before and during at least a part of the application procedure without help from the at that time removed protection layer 5, the foam need to be rather thick in order to have a required form stability. The thickness of the foam shall be between 0.5 mm-10 mm, preferably between 0.75-7 mm, and most preferably between 1-5 mm. For determination of material thickness, the SS-EN: ISO 9073-2 Method A: 1996 was used.

The stiffening layer 4 can be applied onto the film layer 2 by the application of heat and/or pressure or be glued thereto.

The foam used in the stiffening layer 4 has preferably closed cells. Such a foam presents a larger contact surface to the film 2 than a foam having open cells. Thereby the foam is easier to attach to the film in a controlled manner so that the force needed to remove the stiffening layer from the film after application of the film to skin will have the desired magnitude. The force needed to remove the stiffening layer from the film will also be more even over the whole surface attached to the film 2 when the foam used has closed cells than when the foam used has open cells. A user would therefore feel more comfortable to remove a stiffening layer consisting of foam with closed cells than foam with open cells.

Foam with open cells absorbs liquids. If a glue in liquid form is used for attaching a stiffening layer 4 consisting of a foam with open cells to the film 2, it can be hard to determine the amount of glue needed in order to attain a desired removal force. Furthermore, the amount of glue necessary will be larger than if a foam having closed cells were used instead. Thus, although a foam with open cells could be used it is more advantageous to use a foam with closed cells for the stiffening layer since it is easier to control the attachment of the stiffening layer to the film when a foam with closed cells is used.

Examples of suitable foam materials for the present invention are Alveolit® TA 3001 and Alveolit® TEE 3002, both physically cross-linked, closed-cell polyolefin foams, and Alveo-Soft® SAVM200503.00, cross-linked polyolefin soft foam with partly open-cell structure, which all can be obtained from SEKISUI ALVEO AG, Luzern, Switzerland.

Other porous materials than foams can be used in stiffening layers according to the present invention. By "porous material" is in this application meant a material having several small, distributed voids within its volume independent of whether the voids are closed or not. It is believed that the presence of voids within the volume of the material in the stiffening layer contributes to the ability of the stiffening layer to follow the shape of an uneven portion of body of the patient when the dressing is applied. Therefore, for example fibrous materials can be used for stiffening layers according to the present invention. An example of suitable fibrous materials is nonwoven materials having a high porosity.

In order to facilitate the attachment of such materials to the film of the wound dressing or other medical device so that an even and easily pre-determined removal force is obtained for the stiffening layer, such materials can be laminated to a plastic film on the side thereof which is to be turned against the film of the dressing. The attachment of a plastic film to the film of the dressing is easy to control so that the removal force will be even over the surface of the stiffening layer and suitably high. Such a plastic film for facilitating attachment can also be used when the stiffening layer includes a foam with open cells.

The porosity of foam or other porous materials used in the stiffening layer should preferably be at least 80%, more preferably at least 90% and most preferably at least 95%.

The stiffening layer covers the whole area of the film, which ensures support and protection of the during handling of dressing from manufacture to application thereof to a wound. A cut line 6 is dividing the stiffening layer 4 into a central portion 7 and a frame portion 8. If the person who is to affix such a dressing to a patient deems it convenient he or she can remove the central portion before applying the dressing, preferably before removal of the protection layer. Such a stiffening layer has also the advantage of enabling the dressing 1 to be cut into two or more smaller film dressings without portions of the film becoming uncovered by stiffening material.

The stiffening layer according to the present invention can of course also be dived by cutting lines into several other portions than a central portion and a frame, for example can two cutting lines run diagonally dividing the stiffening layers into several portions and a cutting line or cutting lines can also divide the stiffening layer 4 shown in FIG. 1 into two or several portions.

The stiffening layer and of course also the protection layer can be provided with one or more grip tabs or the like for facilitating removal of these layers.

The choice of materials in a wound dressing or other medical device according to the present invention is preferably such that sterilization is possible, for example by ethylene oxide.

The embodiments described above can of course be modified without leaving the scope of invention. Other medical devices than wound dressings and ostomy bags and bandages, such as incision films and surgical drapes, can be provided with a stiffening layer in accordance with the invention, for example a fixation tape. Other adhesives, such a hot-melt or acrylate based adhesives can be used instead of silicone adhesives. The adhesive need not cover the whole surface of the film and can be applied as a continuous or discontinuous layer. The dressings can have another shape than the dressing according to FIGS. 1 and 2, and can be of another type, for example a so called island dressing including a wound pad. Furthermore, other plastic materials than polyurethane, for example polyethylene, polyester, or silicone, can be used as adhesive coated film layer in the wound dressing or other medical device according to the present invention. The invention shall therefore only be limited by the content of the enclosed patent claims.

The invention claimed is:

1. A wound dressing or other medical device, comprising:
    a plastic film having a first and second side, wherein said first side is provided with a layer of self-adhering adhesive; and
    a stiffening layer removably attached to said second side of said plastic film, wherein said stiffening layer comprises a stretchable material having a thickness of between 0.5 mm to 10 mm, wherein said stiffening layer covers a whole area of said second side of said plastic film and is divided into two or more portions by at least one cutting line.

2. The wound dressing of claim 1, wherein the stiffening layer has a stretchability of less than 2000 kN/m$^2$.

3. The wound dressing of claim 2, wherein the stiffening layer comprises elastic material.

4. The wound dressing of claim 3, wherein the stiffening layer comprises polymeric foam.

5. The wound dressing of claim 4, wherein the foam is a polyurethane foam or a polyethylene foam.

6. The wound dressing of claim 5, wherein the foam has closed cells.

7. The wound dressing of claim 2, wherein the stiffening layer comprises a layer of fibrous material.

8. The wound dressing of claim 2, wherein the stiffening layer comprises a first layer of fibrous material or polymeric foam with open pores, and a second layer of plastic film laminated to the first layer.

9. The wound dressing of claim 1, wherein the stiffening layer comprises a porous layer.

10. The wound dressing of claim 9, wherein the porous layer has a porosity of at least 80%.

11. The wound dressing of claim 9, wherein the porous layer has a porosity of at least 90%.

12. The wound dressing of claim 9, wherein the porous layer has a porosity of at least 95%.

13. The wound dressing of claim 1, wherein the stiffening layer is removably attached to the second side of the plastic film by application of heat and pressure.

14. The wound dressing of claim 1, wherein the stiffening layer is removably attached to the second side of the plastic film by a layer of adhesive.

15. The wound dressing of claim 1, wherein the stretchability of the stiffening layer is less than 1000 kN/m$^2$.

16. The wound dressing of claim 1, wherein the stretchability of the stiffening layer is less than 500 kN/m$^2$.

17. The wound dressing of claim 1, wherein the stretchability of the stiffening layer is less than 250 kN/m$^2$.

18. The wound dressing of claim 1, wherein the cutting line divides the stiffening layer into a central portion and a frame portion.

* * * * *